United States Patent [19]

Strade

[11] 4,004,005
[45] Jan. 18, 1977

[54] STEROIDAL ERYTHROPOIETIC AGENTS AND THERAPEUTIC COMPOSITIONS AND METHODS

[75] Inventor: Henry A. Strade, Montville, N.J.

[73] Assignee: Akzona Incorporated, Asheville, N.C.

[22] Filed: Sept. 30, 1975

[21] Appl. No.: 618,176

[52] U.S. Cl. .............................................. 424/243
[51] Int. Cl.² ................ A61K 31/56; A61K 31/575
[58] Field of Search .................................... 424/243

[56] References Cited

OTHER PUBLICATIONS

Floch et al. – Chem. Abst., vol. 58 (1963) p. 4783d.

*Primary Examiner*—Sam Rosen
*Attorney, Agent, or Firm*—Francis W. Young; Hugo E. Weisberger

[57] ABSTRACT

The stimulation of erythropoesis in humans and other warm-blooded animals is produced by administration of an effective amount of a compound selected from the group consisting of 3α-hydroxy-5β-estrane-17-one and the 3-esters and 3-ethers thereof, preferably 19-noretiocholanolone. The steroids are particularly advantageous in that they exhibit an unexpected low level of pyrogenicity as compared to etiocholanolone, a known pyrogen.

7 Claims, No Drawings

STEROIDAL ERYTHROPOIETIC AGENTS AND THERAPEUTIC COMPOSITIONS AND METHODS

BACKGROUND OF THE INVENTION

This invention relates to novel non-pyrogenic steroidal erythropoietic agents, and to therapeutic compositions containing the same and methods of treatment. More particularly, the invention concerns 19-noretiocholanolone and derivatives thereof, and their application in the stimulation of erythropoiesis.

Erythropoiesis is the process of formation of red blood cells.

The term anemia implies an abnormally low number of circulating red cells or a decreased concentration of hemoglobin in the blood. The appearance of anemia reflects either marrow failure or excessive red cell loss, or both. Marrow failure, i.e., reduced erythropoiesis, may occur as a result of a nutritional deficiency, toxic exposure, tumor invasion, or other and sometimes unknown causes.

For the treatment of anemias of bone marrow failure (hypoplastic and aplastic anemias), it has been proposed to use substances which might stimulate the marrow, such as androgens or corticosteroids. Campbell et al U.S. Pat. No. 3,383,282 discloses various 3,5-androstadiene-3,17-diol derivatives as possessing erythropoietic activity. Schmidlin et al U.S. Pat. Nos. 3,519,659 and 3,519,660 disclose various prednisolone derivatives having antileukemia activity.

It is known that erythropoietic activity is exhibited by metabolites of certain androgenic, anabolic, or progestational steroids. Thus, Levere et al. Proceedings of a Symposium held in conjunction with the American Society of Hematology, Dec. 4, 1971, Chapter III, discloses that etiocholanolone, a human metabolite of testosterone, possesses erythropoietic activity. Jepson, ibid., Chapter II, discloses that nandrolone (19-nortestosterone; 17-β-hydroxy-19-nor-4-androsten-3-one), an anabolic steroid, possesses erythropoietic activity similar to testosterone. This substance, however, has the drawback of exhibiting androgenic side-effects. It is known in the form of its decanoate, described in De-Witt et al U.S. Pat. No. 2,998,423. Etiocholanolone possesses the substantial drawback of being a pyrogen in man.

GENERAL DESCRIPTION OF THE INVENTION

In accordance with the present invention, it has been found that certain estrane derivatives which contain the 5β-H configuration exhibit erythropoietic activity, while at the same time they are nonpyrogenic and exhibit little or no androgenic side effects.

The compounds found to be non-pyrogenic and active in stimulating erythropoiesis are 19-noretiocholanolone (3α-hydroxy-5β-estrane-17-one), and 3-esters and 3-ethers.

19-Noretiocholanolone is a known compound and is disclosed by Engel et al, J. Biol. Chem. 231, 1, 159 (1958). This compound is also disclosed in an article by Counsell in Tetrahedron, Vol. 15, 202–211 (1961). 19-noretiocholanolone may also be synthesized by hydrogenating nandrolone 17-acetate to the corresponding 5 -3keto-17β-acetate by the method described in J. Org. Chem. 31. 2394 (1966), then hydrogenating the 3-keto group to form the 3α-hydroxy group using lithiumaluminum tri-tert.-butoxyhydride, protecting the 3α-hydroxy group and hydrolyzing the 17β-acetate to 17-keto with $CrO_3$-pyridine, and finally removing the 3α-protecting group.

The 3-esters of the aforementioned compounds which exhibit erythropoietic activity include those of pharmaceutically acceptable acids, which may be either inorganic or organic. Examples of inorganic acids include hydrochloric, sulfuric, and phosphoric, while saturated or unsaturated organic carboxylic acids having 1 to 18 carbon atoms may also be employed. The preparation of these esters can be carried out in conventional manner by reacting the 3α-hydroxy steroid with the acid, or with its corresponding anhydride or acyl halide.

As examples of organic carboxylic acids, mention is made of the following: formic, acetic, propionic, butyric, valeric, capric, decanoic, undecylic, lauric, tridecyclic, myristic, oleic, palmitic, stearic, trimethylacetic, diethyl acetic, cyclohexane carboxylic, cyclopentylpropionic, cyclohexylbutyric, cyclohexylpropionic, undecylenic, benzoic, phenylacetic, phenylpropionic, phenylbutyric, malonic, succinic, glutaric, pimelic, and tartaric acids.

The 3α-hydroxy steroid may be etherified with a group derived from an aliphatic, aromatic, araliphatic, or heterocyclic hydrocarbons. Examples of suitable ether groups include methoxy, ethoxy, propoxy, benzyloxy, and phenylethoxy.

The preferred erythropoietic agents according to the invention are 19-noretiocholanolone and its 3-decanoate ester.

DESCRIPTION OF THE PREFERRED EMBODIMENTS

The following examples illustrate the therapeutic compositions of the invention and their application, but are not to be regarded as limiting.

EXAMPLE 1

Erythropoietin Bioassay 19-noretiocholanolone was administered to mice as a single subcutaneous injection of 2.5 mg. in a 2-propanediol vehicle, at various intervals following induced hypoxia. The first injection was made on the third day post-hypoxia; on the fifth post-hypoxic day, $0.5\mu$ $Ci^{59}FeCl_3$ was injected intravenously; the percent $^{59}Fe$-incorporation into the red cells was determined on day 7 post-hypoxia. The 19-noretiocholanolone stimulated radioiron incorporation significantly, the figure for % RBC-$^{59}Fe$ incorporation being $5.82 \pm 1.21$ ($p<0.05$).

EXAMPLE 2

Rat Marrow Bioassay 19-noretiocholanolone was added in 1 $\mu$l of 2-propanediol to rat bone marrow, (S-D ♂ ♂, ~100 - 150 g.) at the initiation of the cultures; about 72 hours later 0.5 $Ci^{59}Fe$, bound to transferrin, was added to the cultures; radioheme was extracted 6 hours later and quantitated. The data suggest that 19-noretiocholanolone is active in this system:

| Concentration (M) | $3\times10^{-7}$ | $3\times10^{-8}$ | $3\times15^{-9}$ | $3\times10^{-10}$ |
|---|---|---|---|---|
| | 54 | 46 | 172 | 180±47.9 |

EXAMPLE 3

14C-Labeled Hemoglobin

Human marrow cultures were treated with 19-noretiocholanolone for three days; $3\mu$Ci of $^{14}$C-valine was added for the last 24 of culture. Hemoglobin was isolated simultaneously from cells cultured with either 2-propanediol or the steroid ($3 \times 10^{-10}$M). The specific activity ($^{14}$C-cpm/A$_{540}$) of each was calculated and the ratio determined. The data show that the steroid was stimulatory:

| | $^{14}$C-hemoglobin[1] |
|---|---|
| 19-noretiocholanolone | 1.34 |

[1]ratio of the specific activity of a steroid-treated culture to a 2-propanediol-treated culture.

EXAMPLE 4

Human Marrow Cultures

Radioiron incorporation into heme was determined in the same manner as in the rat marrow cultures of Example 2. The 19-noretiocholanolone was evaluated at a concentration of $3\times10^{-8}$M except in the marrow obtained from a patient with no demonstrable disease where a concentration of $5\times10^{-10}$M was used. The test data are as follows:

| % Fe-Heme Incorporation | | | | |
|---|---|---|---|---|
| No Demonstrable Disease | Systemic Lupus Erythrematosus | Mycosis Fungoides | Hemolytic Anemia | Rhabdomyosarcoma |
| 90[1] | 144 | 148 | 93 | 105 |

[1]The vehicle is considered as 100%.

The foregoing data indicate that 19-noretiocholanolone stimulates erythropoesis both in vivo and in vitro.

The foregoind compounds are adapted for the administration thereof to humans and other warm-blooded animals in amounts effective to stimulate erythropoesis, such amounts being generally in the range from about 5 to about 500 mg. per unit dosage. The usual method of administration is parenterally, for which purpose the compound may be prepared in a form suitable for injection as a solution or suspension in m ml. ampoules. The following is an example of such a preparation.

EXAMPLE 5

Ampoule Dosage Form

The dosage form can be prepared by admixing 500 g. of 19-noretiocholanolone or its 3-esters or ethers into 2 liters of sterile sesame oil containing about 500 ml. of benzyl alcohol as a preservative, and heating the resulting mixture to about 80° C. to obtain a solution. The solution is allowed to return to room temperature and the volume is increased to 10 liters by addition of sesame oil. The solution is filtered through a bacteriological membrane filter and is packaged into dosage forms, e.g., vials of 2 or 5 ml. or ampoules of 1 ml. The strength of the steroid solution is about 50 mg./cc.

What is claimed is:

1. Method for the stimulation of erythropoesis in humans and other warm-blooded animals in need of such therapy which comprises administering an amount effective to produce such stimulation of a compound selected from the group consisting of 3$\alpha$-hydroxy-5$\beta$-estrane-17-one and the 3-esters of organic carboxylic acids and 3-ethers thereof in which the ether group is selected from the group consisting of methoxy, ethoxy, propoxy, benzyloxy and phenylethoxy.

2. The method of claim 1 in which said compound is 19-noretiocholanolone.

3. The method of claim 1 in which said compound is administered parenterally.

4. The method of claim 1 wherein the compound is the 3-decanoate ester of 19-noretiocholanolone.

5. A pharmaceutical composition in unit dosage form adapted for parenteral administration for the stimulation of erythropoesis in humans and other warm-blooded animals, containing as its active ingredient an effective amount within the range from about 5 to 500 mg. per dosage unit of a compound selected from the group consisting of 3$\alpha$-hydroxy-5$\beta$-estrane-17-one, and the 3-esters of organic carboxylic acids and 3-ethers thereof in which the ether group is selected from the group consisting of methoxy, ethoxy, propoxy, benzyloxy and phenylethoxy.

6. The preparation of claim 5 in which said compound is 19-noretiocholanolone.

7. The preparation of claim 5 in which said compound is the 3-decanoate ester of 19-noretiocholanolone.

* * * * *